United States Patent
Frisa et al.

(10) Patent No.: US 6,755,786 B2
(45) Date of Patent: Jun. 29, 2004

(54) ULTRASONIC DIAGNOSTIC IMAGING WITH ELEVATION BIPLANE IMAGES

(75) Inventors: Janice Frisa, Atkinson, NH (US); McKee Dunn Poland, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/448,517

(22) Filed: May 30, 2003

(65) Prior Publication Data

US 2003/0195422 A1 Oct. 16, 2003

Related U.S. Application Data

(63) Continuation of application No. 10/437,834, filed on May 12, 2003, which is a continuation-in-part of application No. 10/231,704, filed on Aug. 29, 2002, which is a continuation-in-part of application No. 09/641,306, filed on Aug. 17, 2000, now Pat. No. 6,443,896.

(51) Int. Cl.[7] .................................................. A61B 8/12
(52) U.S. Cl. ..................................................... 600/443
(58) Field of Search ................................ 600/443, 447, 600/459, 445; 73/606; 128/916; 345/419

(56) References Cited

U.S. PATENT DOCUMENTS

| | | | | |
|---|---|---|---|---|
| 5,546,807 A | * | 8/1996 | Oxaal et al. | 73/606 |
| 5,546,946 A | * | 8/1996 | Souquet | 600/459 |
| 5,608,849 A | * | 3/1997 | King, Jr. | 345/419 |
| 6,099,474 A | * | 8/2000 | Solek | 600/459 |
| 6,241,675 B1 | * | 6/2001 | Smith et al. | 600/443 |
| 6,245,017 B1 | * | 6/2001 | Hashimoto et al. | 600/447 |
| 6,413,219 B1 | * | 7/2002 | Avila et al. | 600/443 |
| 6,443,896 B1 | * | 9/2002 | Detmer | 600/445 |

* cited by examiner

Primary Examiner—Mary Beth Jones
Assistant Examiner—Ruby Jain
(74) Attorney, Agent, or Firm—W. Brinton Yorks, Jr.

(57) ABSTRACT

An ultrasonic diagnostic imaging system is described in which two planes of a volumetric region which are in different elevation planes are scanned in real time. In one embodiment the two planes are scanned in the sector format with a common apex, causing corresponding depths of the two images to be separated by the same distance in elevation. In another embodiment one image plane has a fixed orientation with respect to the imaging probe and the location of the other image plane can be adjusted by the user.

11 Claims, 4 Drawing Sheets

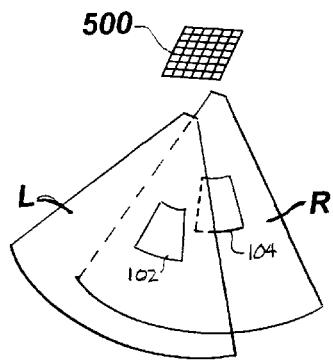
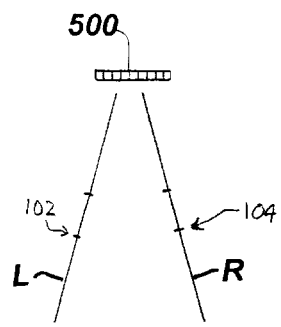
FIG. 2A  FIG. 2B
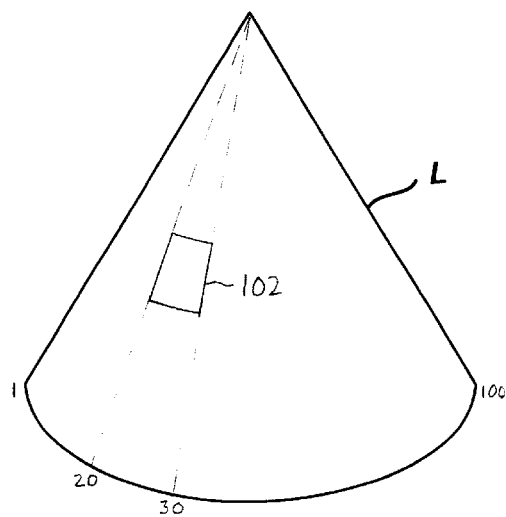
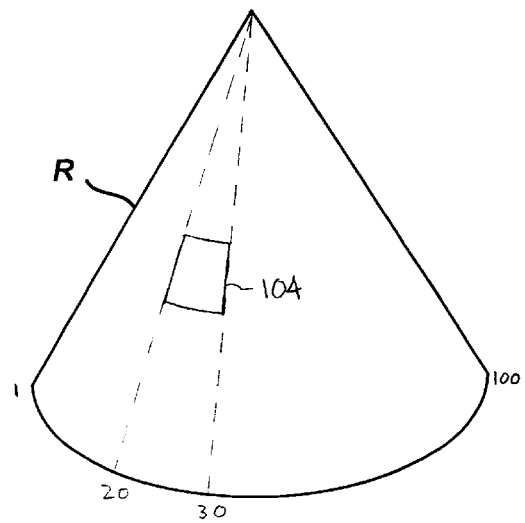
FIG. 3

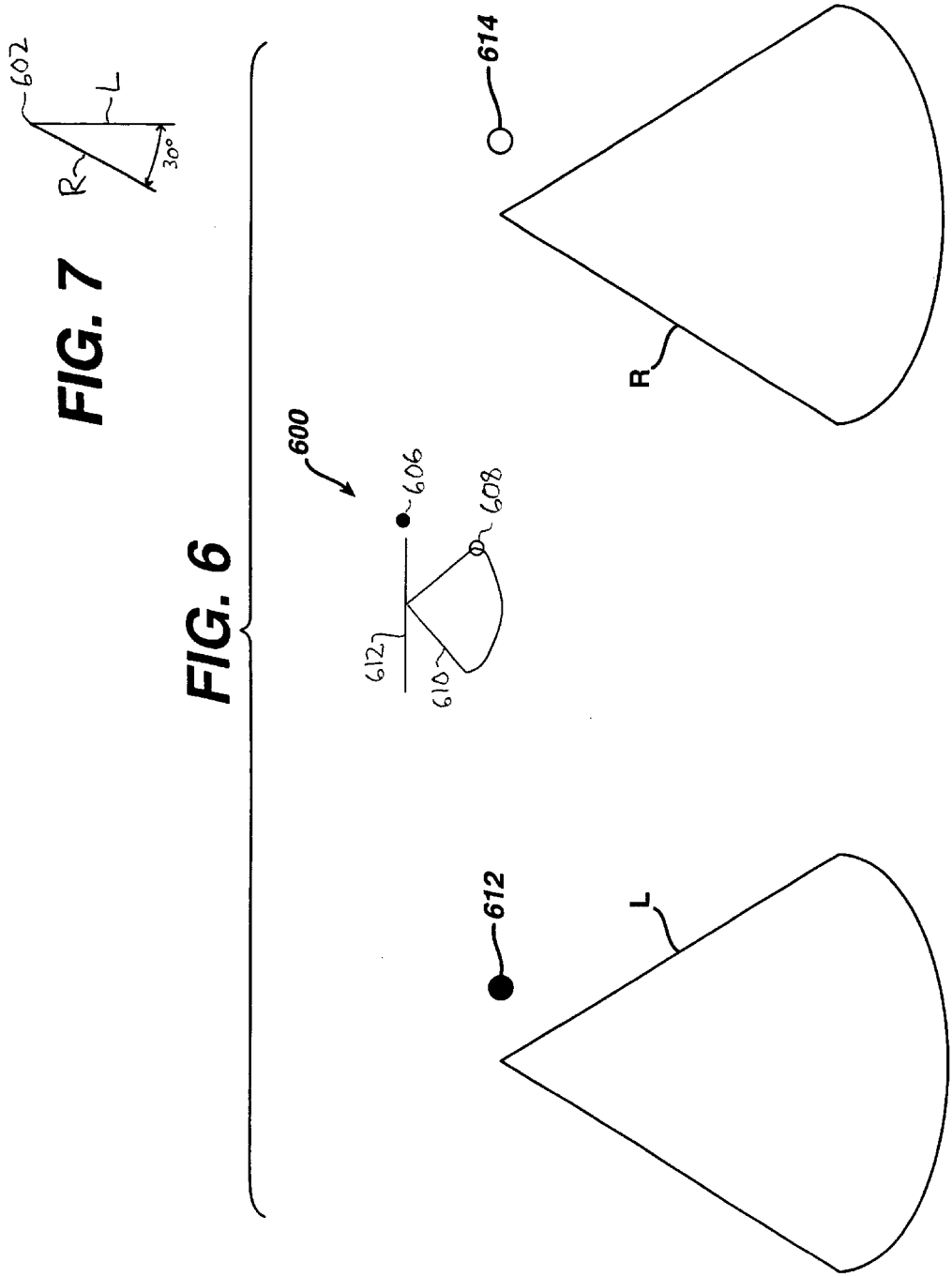

ULTRASONIC DIAGNOSTIC IMAGING WITH ELEVATION BIPLANE IMAGES

This is a continuation in part application of U.S. patent application Ser. No. 10/437,834, filed May 12, 2003, which is a continuation in part application of U.S. patent application Ser. No. 10/231,704, filed Aug. 29, 2002, which is a continuation in part application of U.S. patent application Ser. No. 09/641,306, filed Aug. 17, 2000 and now U.S. Pat. No. 6,443,896.

This invention relates to medical ultrasonic imaging, and more particularly, to ultrasonic imaging systems and methods for the simultaneous imaging of motion in two or more planes of a volumetric region of the body.

U.S. patent describes the use of a two dimensional array probe to ultrasonically scan two planes of a volumetric region of the body simultaneously in real time. The two dimensional array enables beams to be transmitted and focused electronically in any direction through the volumetric region opposing the array transducer. This means that two or more image planes in the region can be scanned at a rapid enough rate for the production of simultaneous real-time images of both image planes. This mode of operation is referred to as the "biplane" mode. The biplane mode is an effective way to image a 3D region of the body when a true three dimensional image may be difficult to interpret. Planar (two dimensional) images are more familiar to most diagnosticians, and two image planes makes it possible to image an organ from several different viewpoints at the same time. It is very useful when the clinician is able to adjust the relative positions of the two image planes when surveying the anatomy of interest. In the biplane mode as discussed in this patent, one of the image planes is always oriented normal to the center of the array probe, in the same manner as is the image plane of a conventional one dimensional array used for two dimensional imaging. This plane is referred to as the reference plane. The other image plane can be manipulated by the clinician in several different ways. One is to rotate the second image plane with respect to the reference image. In the rotate mode, the two images share a common center line and the second image can be rotated around this center line, meaning that the second image plane can be co-planar with the reference image, oriented at 90° with respect to the reference image, or at any angular orientation between 0° and 90°. The other biplane mode discussed in the patent is the tilt mode. In the tilt mode the center line of the second image is common with one of the s canlines of the reference image. The common line can be varied so that the second image can intersect the center of the reference image, either of the most lateral scanlines of the reference image, or any scanline in between. However, other planar orientations besides those of the rotate and lateral tilt biplane modes may also be useful in a particular clinical situation, better providing images that the clinician needs for diagnosis. These orientations may be useful in B mode imaging and in Doppler imaging.

In accordance with the principles of the present invention, the relative orientation of two or more image planes in a volumetric region can be varied in the elevation dimension. In one embodiment the position of a reference image is held stationary with respect to the probe and a second image is varied elevationally with respect to the reference image. The two images can be co-planar or located in elevationally separate image planes. In another embodiment the two planes maintain a common apex and the second image is tilted elevationally with respect to the reference plane so that a common depth is at a common distance from the other plane. In yet another embodiment the two images both have a color box at the same respective coordinates of the image. A single control can be used to adjust the size or location of the two color boxes in the two images in the same way.

In the drawings:

FIGS. 2A and 2B illustrate two views of two elevationally different image planes with color boxes;

FIG. 3 illustrates a system display of two image planes in the elevation biplane mode in accordance with the principles of the present invention;

FIG. 6 illustrates a biplane display and image orientation icon for operation in the "elevation tilt" mode; and FIG. 7 is an edge-on illustration of the two image planes of FIG. 6.

Figure 1:
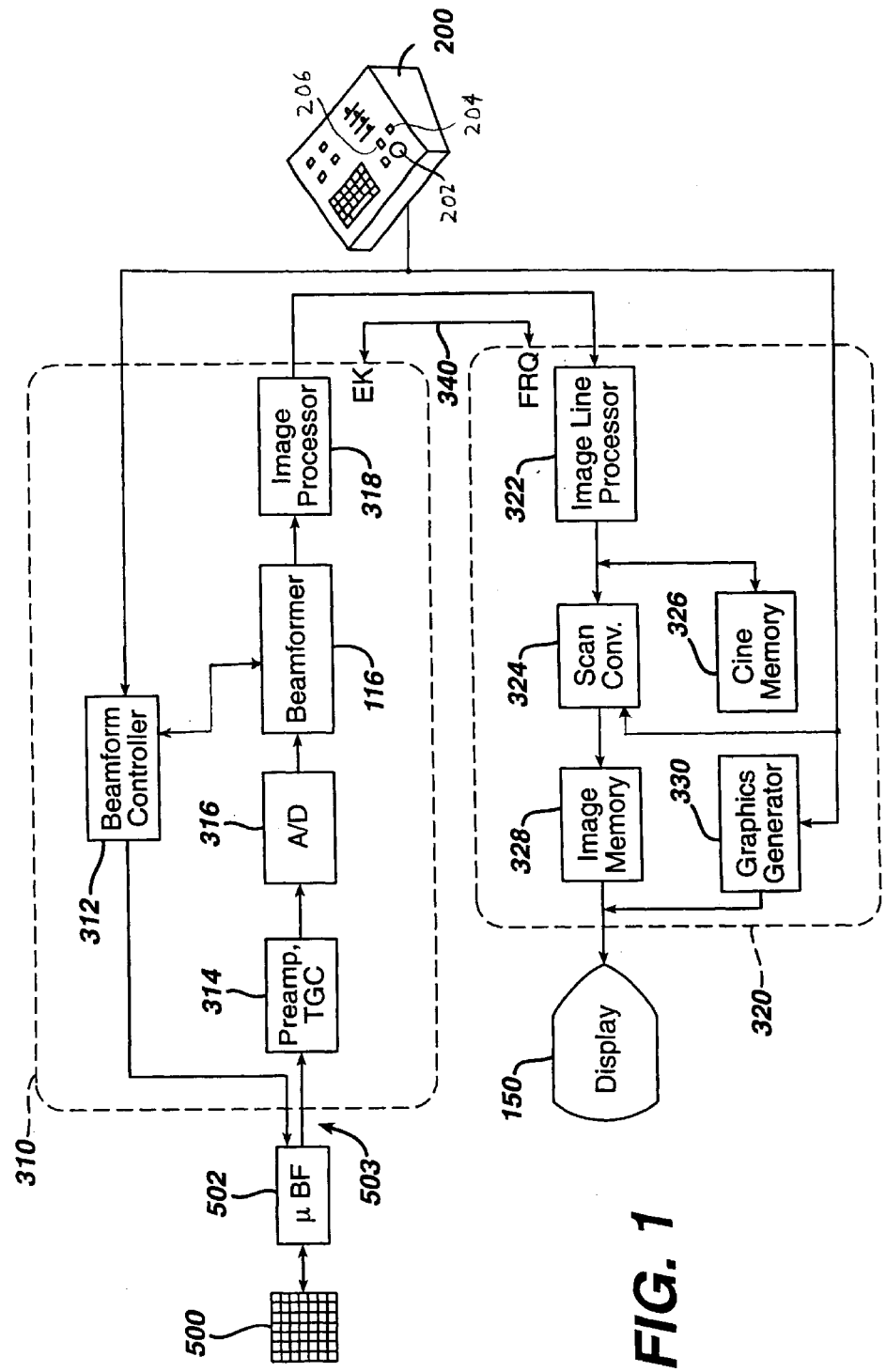
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. A probe includes a two dimensional array transducer 500 and a micro-beamformer 502. The micro-beamformer contains circuitry which control the signals applied to groups of elements ("patches") of the array transducer 500 and does some processing of the echo signals received by elements of each group. Micro-beamforming in the probe advantageously reduces the number of conductors in the cable 503 between the probe and the ultrasound system and is described in U.S. Pat. No. 5,997,479 (Savord et al.) and in U.S. Pat. No. 6,436,048 (Pesque).

The probe is coupled to the scanner 310 of the ultrasound system. The scanner includes a beamform controller 312 which is responsive to a user control 200 and provides control signals to the micro-beamformer 502 instructing the probe as to the timing, frequency, direction and focusing of transmit beams. The beamform controller also control the beamforming of received echo signals by its coupling to analog-to-digital (A/D) converters 316 and a beamformer 116. Echo signals received by the probe are amplified by preamplifier and TGC (time gain control) circuitry 314 in the scanner, then digitized by the A/D converters 316. The digitized echo signals are then formed into beams by a beamformer 116. The echo signals are then processed by an image processor 318 which performs digital filtering, B mode detection, and Doppler processing, and can also perform other signal processing such as harmonic separation, speckle reduction through frequency compounding, and other desired image processing.

The echo signals produced by the scanner 310 are coupled to the digital display subsystem 320, which processes the echo signals for display in the desired image format. The echo signals are processed by an image line processor 322, which is capable of sampling the echo signals, splicing segments of beams into complete line signals, and averaging line signals for signal-to-noise improvement or flow persistence. The image lines are scan converted into the desired image format by a scan converter 324 which performs R-theta conversion as is known in the art. The image is then stored in an image memory 328 from which it can be displayed on a display 150. The image in memory is also overlayed with graphics to be displayed with the image, which are generated by a graphics generator 330 which is responsive to a user control. Individual images or image sequences can be stored in a cine memory 326 during capture of image loops.

For real-time volumetric imaging the display subsystem 320 also includes the 3D image rendering processor (not shown) which receives image lines from the image line processor 322 for the rendering of a real-time three dimensional image which is displayed on the display 150.

In accordance with the principles of the present invention, two images, referred to herein as biplane images, are acquired by the probe in real time and displayed in a side by side display format. Since the 2D array 500 has the ability to steer transmitted and received beams in any direction and at any inclination in front of the array, the planes of the biplane image can have any orientation with respect to the array and to each other. In one embodiment the two image planes are separated in the elevation dimension as shown by the perspective view of planes L and R in FIG. 2A. In FIG. 2B the same planes L and R are viewed "edge-on." In each instance the two dimensional array transducer 500 is shown positioned above the image planes. In these examples the image format is the sector image format, with the image lines emanating from a common apex at or near the transducer 500. However, linear or steered linear scan formats can also be employed, as will be shown below.

In other embodiments the elevation biplane images L and R each include an area where motion is displayed. This can be done by Doppler processing the signals received from areas where motion is to be displayed, and displaying the area with a color (velocity) Doppler or power Doppler overlay of the B mode image. Other alternatives such as correlating temporal echo information and moving target indicators may also be used. See, e.g., U.S. Pat. No. 4,928, 698 and U.S. Pat. No. 5,718,229. The area where motion such as blood flow or tissue motion is to be displayed may be outlined by a color box 102, 104 as shown in FIG. 2A. For ease of use the color boxes 102, 104 on the two image planes may be aligned in range (depth) and azimuth in the two planes, and their manipulation and adjustment controlled in tandem by a single set of user controls. This enables a region of interest (ROI) in the volume being scanned to be viewed by two planes separated in the elevation direction. As used herein, two images are separated in the elevation direction if they do not share the same image plane, that is, they are not co-planar within the subject being imaged. This capability is useful, for example, when examining an ROI on a particular side of the volume. It is also useful when measuring the extent of a jet from a heart valve in the elevation direction. The reference plane can be placed near the valve to intercept the jet in close proximity to the valve and the adjustable plane moved to intercept the jet at its greatest detectable range from the valve, for instance. When the user controls are manipulated to position the color box 102 to intercept the jet near the valve, the color box 104 of the second plane will automatically be positioned in alignment with the color box 102.

In the embodiment of FIG. 1, a trackball 202 and two keys 204 and 206 on the ultrasound system control panel 200 can be used to manipulate and adjust the color boxes 102, 104 in the elevation planes L and R. When the ultrasound system is in the elevation biplane mode and the Position key 204 is depressed, moving the trackball 202 will move the color boxes in tandem in the two images L and R. Since the trackball can be rolled in any direction, the color boxes can be repositioned together in any direction with the trackball control. The sizes of the color boxes can be changed by depressing the Size key 206, after which movement of the trackball will cause the width or height of the color boxes to be enlarged or reduced, depending upon the direction of trackball motion. For instance, rolling the trackball to the left will expand the width of the color boxes, and rolling the trackball to the right will decrease the width of the color boxes. By use of the two keys 204, 206 and the trackball 202, the color boxes can be sized and positioned together to meet the needs of a particular clinical examination. This common adjustment can be identical, which will usually be the case for image planes which do not intersect or are parallel. The common adjustment can also be proportionally controlled. For example, the adjustment of a color box can be made proportional to the cosine of the angle between the two image planes so as to keep the regions of interest of the color boxes approximately lined up in the medium being imaged. The adjustment of the color boxes is in this example a function of the relative orientation of the two image planes.

The manner in which the ultrasound system of FIG. 1 scans different planes with color boxes is illustrated in FIG. 3 with reference to FIG. 1. The user manipulates a user control on the control panel 200 such as the trackball to position the second plane R in a desired orientation with respect to the reference plane L. This may conveniently be done with reference to an icon which graphically illustrates the respective positions of the two elevation planes as described in U.S. patent, entitled "IMAGE ORIENTATION DISPLAY FOR A THREE DIMENSIONAL ULTRASONIC IMAGING SYSTEM." The beamformer controller 312 responds to the user selection of the image planes by programming the sequence of scanlines to be transmitted by the beamformer 116 or the microbeamformer 502 in a frame table. The beamformer controller reprograms a frame table for both images by recalculating or selecting the proper sequence of focusing coefficients for transmit and receive beamforming. The transmit beams are transmitted and focused in the desired directions through the volume in front of the transducer array 500 under control of the transmit beamformer in the microbeamformer or the beamformer. FIG. 3 illustrates the sequences of scanlines for images of 100 scanlines each, with the color boxes 102 and 104 sized and positioned between scanlines 20 and 30. In that instance each image L and R is acquired by transmitting individual B mode lines along each of scanlines 1–19. For lines 20 to 30 an ensemble of Doppler pulses is transmitted along each scanline as well as a B mode pulse for the structural image. The ensemble of Doppler pulses is generally six to sixteen pulses in length, depending upon the desired resolution and the speed of the motion to be detected. A single pulse can be used for the B mode pulse and one of the Doppler ensemble pulses as described in U.S. Pat. No. 6,139,501, if desired. Pulses of the ensembles can be time-interleaved among the different scanlines and the B mode pulses if desired. After the echoes for these lines are acquired B mode pulses are transmitted along the remaining scanlines 31–100. This sequence of transmission and echo reception can be used for both the L and R images, with only the beam steering directions being different from one image to the other, allowing the beamformer controller to use the same sequence twice. It is also possible to time-interleave transmit beams of the two images as discussed in U.S. patent.

The B mode echoes are processed by amplitude detection in the image processor 318, and the Doppler echo ensembles are Doppler processed in the image processor for the production of display signals depicting flow or tissue motion. The processed B mode and Doppler signals are then coupled to the display subsystem 320 for display.

The selection of the desired image planes is also coupled to the display subsystem 320, where the scan converter 324 and the graphics generator 330 are informed of the design of the images. This enables the scan converter to anticipate and then properly locate the Doppler information along the scanlines 20–30 of the specified color box areas 102 and 104, and enables the graphics generator to outline or highlight the color box if desired.

Figure 4:
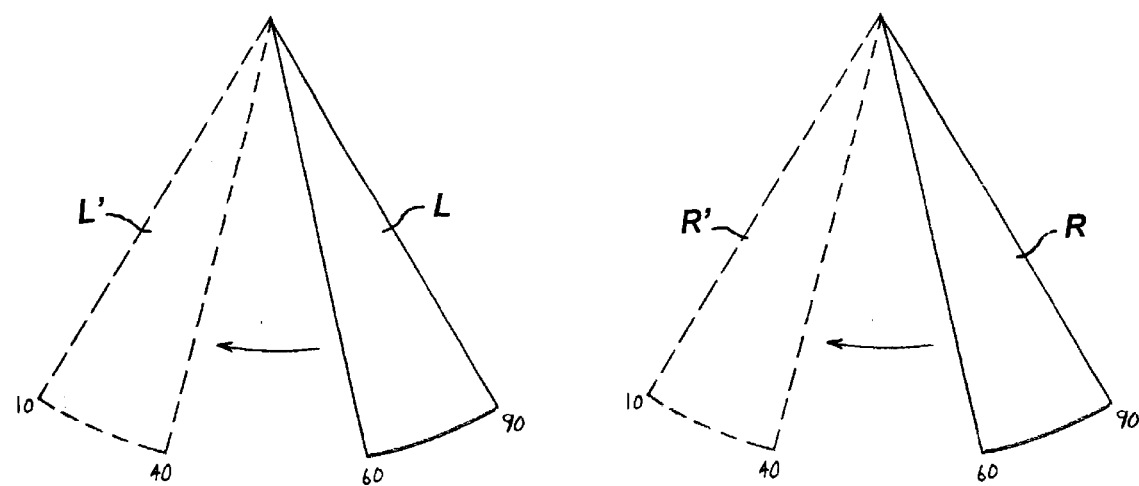
FIG. 4 illustrates the simultaneous relocation of two color boxes in two elevation biplane images.

It is also possible to survey a volume in front of the array transducer by sweeping the image laterally as shown by the screen display of FIG. 4. In the embodiment of FIG. 4 a relatively narrow sector image is formed by transmitting B mode beams along scanlines 60–90 to form each of the L and R images. The sector can be made narrow by selecting the Size key 206 on the control panel and then using the trackball 202 to narrow the sector images. By selecting the Position key 204 the trackball can then be used to simultaneously sweep the two sector images laterally without moving the transducer probe. For example, as indicated by the arrows, the L and R image scan be simultaneously repositioned to the locations of images L' and R', which are scanned by transmitting beams along scanlines 10–40 for each image. This can enable the clinician to move the two elevation sectors from a jet on one side of a heart valve to a jet on the other side of the heart valve, all without moving the probe, for instance. As in the previous example, color boxes can be located in each sector image or the entire sector can be transmitted and received as a color sector.

Figure 5A:
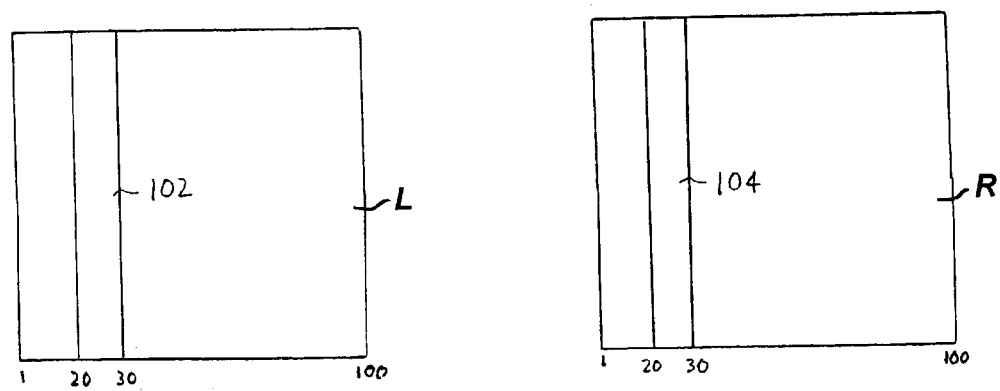
FIG. 5A illustrates two color boxes in rectangularly scanned images.
Figure 5B:
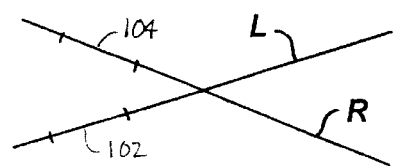
FIG. 5B illustrates one possible orientation of the two images of FIG. 5A.

FIGS. 5A and 5B illustrate the scanning of two rectilinear biplane images L and R which have different elevation orientations. For each image the beamformer controller 312 uses a frame table which directs the transmission and reception of B mode beams along scanlines 1–19, B mode beams and Doppler ensembles along scanlines 20–30, and B mode beams along scanlines 31–100. In another embodiment, steered linear (parallelogram-shaped) images may be transmitted rather than orthogonal rectilinear images. In the embodiment of FIG. 5B the second image R has been separated from the reference image L in the elevation direction and then rotated so that the two images are intersecting within the scanned volume, as shown in this top view from the perspective of the array transducer. The color boxes 102, 104 which are bounded by scanlines 20 and 30 are both seen to be on the left side of the volume being imaged in this embodiment. Elevation separation of the image planes may be optionally combined with rotation of one or both of the planes about an axis such as an image scanline to achieve a desired planar orientation.

FIG. 6 illustrates an elevation biplane display with an image orientation icon 600 which depicts the tilt of the two image planes with respect to each other. This mode of display is referred to herein as the "elevation tilt" mode. The image planes are tilted relative to each other by changing the angle of inclination of at least one of the planes. The images move through selectable positions in which the planes are normal to an arc of variation extending through the planes. Conceptually, it is as if the two L and R sector images are hinged at the apexes and can swing in an arc where the two planes are always separated by the same distance at any given common depth. This motion is illustrated by the edge-on view of the L and R planes in FIG. 7, where the L and R planes have a common apex 602, image L is normal to the plane of the 2D transducer array (not shown), and image R has been tilted to be at a 30° angle from the plane of image L. The orientation icon 600 depicts both image planes as if being viewed from the perspective of the transducer array, and the reference image L is seen as a straight line 612 because it is being viewed edge-on from the top. The image plane R is depicted by sector-shaped icon part 610 which moves above and below the line 612 of the L image as the R image plane is tilted to either side of the L image plane. In this example the L image plane is fixed in orientation so as to always be at 90° to the plane of the transducer array. The two parts of the icon 600 also shown the left-right dots indicating orientation with a correspondingly marked side of the transducer probe. Further details of the icon 600 may be found in parent patent application Ser. No. 10/437,834.

What is claimed is:

1. An ultrasonic diagnostic imaging system comprising:

a two dimensional array transducer which transmits beams in different directions in a volumetric region;

a beamformer coupled to the two dimensional array transducer;

a beamformer controller, coupled to the beamformer, which causes the array transducer to scan only two selected image planes located in different elevation planes with respect to each other, the image planes being separated in elevation, extending from the array transducer and sharing no more than a common apex in the volumetric region;

a scan converter, coupled to the beamformer, which produces real time images of the two image planes; and a display, coupled to the scan converter, which displays the two real time images.

2. The ultrasonic diagnostic imaging system of claim 1, further comprising a user interface for selecting the elevation plane of at least one of the images.

3. The ultrasonic diagnostic imaging system of claim 2, wherein one of the image planes is oriented normal to the face of the two dimensional array transducer, and the elevation plane of the other image planes is selectable by the user interface.

4. The ultrasonic diagnostic imaging system of claim 1, wherein one of the image planes is oriented normal to the face of the two dimensional array transducer.

5. The ultrasonic diagnostic imaging system of claim 1, wherein the elevation planes comprise parallel image planes.

6. The ultrasonic diagnostic imaging system of claim 1, wherein the elevation planes comprise radially separated image planes which are separated by a given angle.

7. The ultrasonic diagnostic imaging system of claim 6, wherein the images comprise sector images.

8. The ultrasonic diagnostic imaging system of claim 2, wherein the user interface further comprises means for adjusting at least one of the position or a dimension of both images simultaneously.

9. The ultrasonic diagnostic imaging system of claim 8, wherein the user interface comprises a trackball.

10. The ultrasonic diagnostic imaging system of claim 9, wherein the user interface further comprises a Size key and a Position key.

11. The ultrasonic diagnostic imaging system of claim 1, wherein the display further comprises means for displaying an icon depicting the relative spatial orientation of the two image planes.

* * * * *